United States Patent
Koehler et al.

(10) Patent No.: US 9,538,970 B2
(45) Date of Patent: Jan. 10, 2017

(54) GENERATING ATTENUATION IMAGE DATA AND PHASE IMAGE DATA IN AN X-RAY SYSTEM

(71) Applicant: KONINKLIJKE PHILIPS N.V., Eindhoven (NL)

(72) Inventors: Thomas Koehler, Norderstedt (DE); Ewald Roessl, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 201 days.

(21) Appl. No.: 14/370,301

(22) PCT Filed: Dec. 26, 2012

(86) PCT No.: PCT/IB2012/057717
§ 371 (c)(1),
(2) Date: Jul. 2, 2014

(87) PCT Pub. No.: WO2013/104966
PCT Pub. Date: Jul. 18, 2013

(65) Prior Publication Data
US 2014/0355740 A1  Dec. 4, 2014

Related U.S. Application Data (60) Provisional application No. 61/585,761, filed on Jan. 12, 2012.

(51) Int. Cl.
*A61B 6/00* (2006.01)
(52) U.S. Cl.
CPC .............. *A61B 6/484* (2013.01); *A61B 6/482* (2013.01)

(58) Field of Classification Search
CPC ......... A61B 6/032; A61B 6/482; A61B 6/484; A61B 6/4291; A61B 6/4035; G01N 2223/419; G01N 23/04; G21K 2207/005
See application file for complete search history.

(56) References Cited

U.S. PATENT DOCUMENTS 6,226,353 B1 *  5/2001  Wilkins .................. A61B 6/484
                                                            378/98.11
2002/0041653 A1  4/2002  Wilkins et al.
(Continued)

FOREIGN PATENT DOCUMENTS

JP      2006334069 A    12/2006
WO   WO2008-006470    1/2008

*Primary Examiner* — Hoon Song (57) ABSTRACT

A system and method for generating phase image data by using the same detector to simultaneously operate in two different modes to simultaneously obtain first and second x-ray image data with different spectral weightings. The first and second x-ray image data respectively include first and second pixel-wise measurement signal values. The detector is configured to obtain the first x-ray image data in a first measurement mode and obtain the second x-ray image data in a second measurement mode different from the first measurement mode for generating the phase image data. The generated phase image data includes pixel-wise phase values from the first and second x-ray image data and is determined by determining a phase value at a pixel from a first measurement signal value obtained in the first measurement mode at the pixel, and from a second measurement signal value obtained in the second measurement mode at the pixel.

18 Claims, 3 Drawing Sheets

(56) References Cited

U.S. PATENT DOCUMENTS

| | | |
|---|---|---|
| 2007/0183560 A1 | 8/2007 | Popescu et al. |
| 2009/0304149 A1 | 12/2009 | Herrmann et al. |
| 2011/0216878 A1 | 9/2011 | Roessl |
| 2012/0153182 A1* | 6/2012 | Iwakiri ................ A61B 6/4283 250/394 |

* cited by examiner

GENERATING ATTENUATION IMAGE DATA AND PHASE IMAGE DATA IN AN X-RAY SYSTEM

CROSS-REFERENCE TO PRIOR APPLICATIONS

This application is the U.S. National Phase application under 35 U.S.C. §371 of International Application Serial No. PCT/IB2012/057717, filed on Dec. 26, 2012, which claims the benefit of U.S. Application Ser. No. 61/585,761, filed on Jan. 12, 2012. These applications are hereby incorporated by reference herein.

FIELD OF THE INVENTION

This invention relates to a method, a computer program and a computer-readable medium for generating phase image data and to an x-ray system.

BACKGROUND OF THE INVENTION

X-ray radiography and tomography are important methods for a variety of applications, for example non-destructive investigation of bulk samples, quality inspection of industrial products and non-invasive examination of anatomical structures and tissue regions of interest in the interior of a patient's body.

X-ray imaging based on attenuation of x-rays may yield excellent results where highly absorbing anatomical structures such as bones are embedded in a tissue of relatively weakly absorbing material. This is due to the fact that the penetration depth of hard x-ray beams may be rather high, which allows for recording sharp projections of the attenuation coefficient.

In US2009/0304149 A1 and US2011/0216878 A1 x-ray imaging system adapted for detecting attenuation based image data are shown.

When different kinds of tissue with similar absorption cross-sections are under examination (for example in mammography or angiography), the contrast of x-ray absorption may be relatively poor. In this case, phase contrast x-ray radiography and tomography may be employed, where the change of phase of the x-rays penetrating the object of interest is examined.

There are several methods to retrieve phase information. Currently, the most popular is a Talbot interferometer type method, which may be grating based. However, there are alternatives, among which the in-line holography approach is appealing because it may not require any optical instruments like monochromators or gratings which need to be aligned carefully.

In WO 2008/006470 A1 an x-ray interferometer for phase contrast imaging is shown.

SUMMARY OF THE INVENTION

One of the objects of the invention is to provide further possibilities to generate phase image data.

This object may be achieved by the subject-matter of the independent claims. Further exemplary embodiments are evident from the dependent claims and the following description.

An aspect of the invention relates to a method for generating phase image data.

According to an embodiment of the invention, the method comprises the steps of: receiving first x-ray image data comprising first pixel-wise measurement signal values; receiving second x-ray image data comprising second pixel-wise measurement signal values; wherein the first x-ray image data was obtained in a first measurement mode and the second x-ray image data was obtained in a second measurement mode different from the first measurement mode. Generally, the method may comprise the step of receiving at least two sets of x-ray image data, wherein each set was obtained with a different measurement mode.

The method comprises the further steps of: determining phase image data comprising pixel-wise phase values from the first and second x-ray image data by determining a phase value at a pixel from a first measurement signal value obtained in a first measurement mode at the pixel and a second measurement signal value obtained in a second measurement mode at the pixel.

The phase and attenuation information in x-ray image data is usually mixed in intensity information or data obtained or detected by a detector, which is stored in x-ray image data. It may be seen as a gist of the invention that the mixed information or data may be separated, when two sets of image data are obtained with different measurement modes, for example at different energies or with different detector types. The separation may be performed based on the fact that there is a functional relationship (usually a function that may be determined with a mathematical model) that maps a phase value (and optionally a attenuation value) at a pixel to an intensity value or measurement signal value. With two measurements based on two different measurement modes, two independent equations may be derived from the functional relationship, which may be solved to get the phase value and/or the attenuation value.

Further aspects of the invention relate to a program element for generating phase image data, which, when being executed by a processor, is adapted to carry out the steps of the method as described in the above and in the following and to a computer-readable medium, in which such a computer program is stored. A computer-readable medium may be a floppy disk, a hard disk, an USB (Universal Serial Bus) storage device, a RAM (Random Access Memory), a ROM (Read Only memory) and an EPROM (Erasable Programmable Read Only Memory). A computer readable medium may also be a data communication network, e.g. the Internet, which allows downloading a program code.

A further aspect of the invention relates to a controller for a x-ray system adapted for performing the method as described in the above and in the following.

A further aspect of the invention relates to an x-ray system. According to an embodiment of the invention, the x-ray system comprises an x-ray source, an x-ray detector and a controller. The x-ray system is adapted to obtain x-ray image data with different measurement modes. The controller is adapted to generate phase image data based on the x-ray image data obtained with different measurement modes. It has to be understood that features of the method as described in the above and in the following may be features of the system or the controller as described in the above and in the following and vice versa.

These and other aspects of the invention will be apparent from and elucidated with reference to the embodiments described hereinafter.

BRIEF DESCRIPTION OF THE DRAWINGS

In principle, identical parts are provided with the same reference symbols in the figures.

DETAILED DESCRIPTION OF EMBODIMENTS

Figure 1:
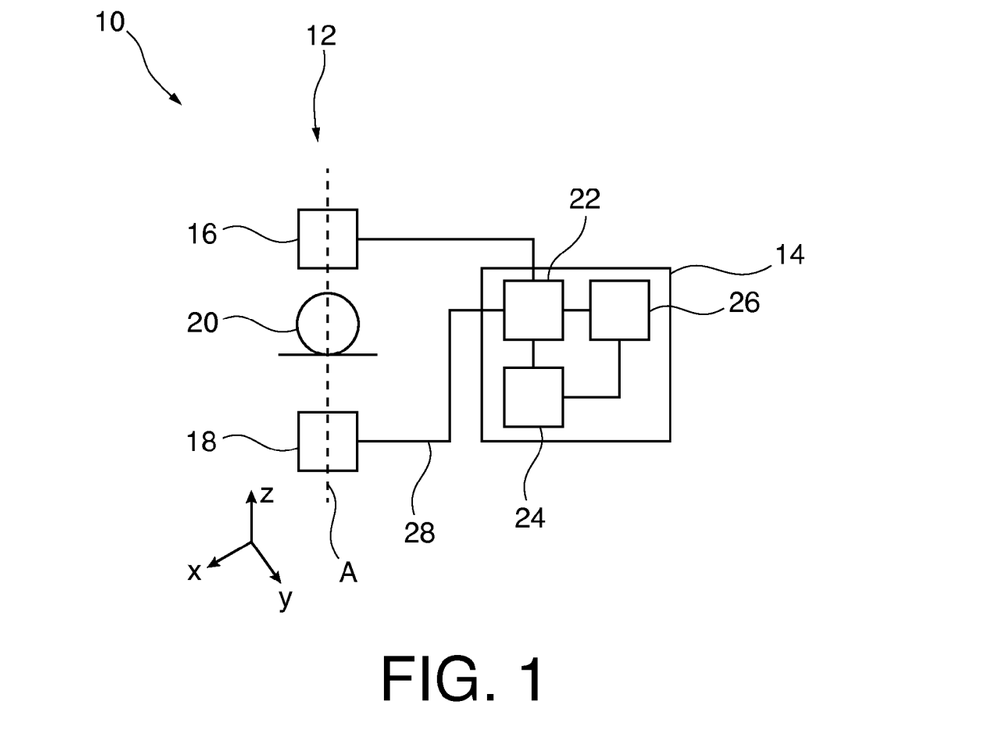
FIG. 1 schematically shows an x-ray system according to an embodiment of the invention.

FIG. 1 shows an x-ray system 10 comprising a detector arrangement 12 and an evaluation unit 14. The detector arrangement 12 comprises an x-ray source 16 and an x-ray detector 18. Between the x-ray source 16 and the x-ray detector 18 an object 20 is placed and x-rays emanating from the x-ray source 16 can penetrate the object 20 and fall onto the detector 18. During the penetration of the object 20, the x-rays are attenuated and shifted in phase. However, the detector 18 may only be adapted to measure an intensity of the x-rays in a pixel-wise manner. For example, the detector 18 is a line detector or a two dimensional detector.

The evaluation unit 14, which may comprise a workstation 14 comprises a controller 22 that is adapted for controlling the x-ray source 16 and the detector 18. For example, the controller 22 may control the duration of the operation of the x-ray source 16 and/or the energy level of the x-rays emanated from the x-ray source 16. Furthermore, the controller 22 may receive image data 28 generated from the x-ray detector 18 during a measurement.

The image data 28 may be processed in processing unit 24 and may be displayed on a HMI 26 with a display. The operation of the x-ray system 10 may be controlled by a human operator via the HMI 26.

In the following different methods are explained that allow separation of absorption and phase shifts in image data. In general, this may be achieved by obtaining image data 28 in different measurement modes. For example, the image data 28 may obtained at different energy levels or with different measurement methods.

For obtaining image data 28 at different energy levels, the x-ray source 16 may be adapted to generate x-rays at different energy levels and/or the detector 18 may be adapted for differentiation between x-rays at different energy levels. In the latter case, the detector 18 may be a spectroscopic detector.

However, image data 28 may also be obtained by detecting the x-rays in different measurement modes, in particular simultaneously during one measurement. This may be achieved by using at least two measurements with different spectral weighting and/or by using a detector 18 that is adapted for operating in 18 measurement modes simultaneously. In these cases, a non-spectroscopic detector 18 like a counting and integrating x-ray (CIX) detector 18 or a integrating and Campbelling x-ray (ICX) detector 18 may be used. These later two examples may be less expensive than a spectroscopic detector. Furthermore, such a detector 18 may produce image data 28 with correlated noise, which may be beneficial for the separation of the absorption and phase contrast.

US2009/0304149 A1 shows a detector that is adapted for counting and integrating.

US2011/0216878 A1 shows a detector that is adapted for integrating and Campbelling.

The spectral weightings are not restricted to highly peaked functions like spectroscopic detectors may have, but also general weightings like the ones valid for CIX of ICX detectors may be used. Thus, the benefit of noise correlation in the different channels of these detectors may be exploited.

Figure 2:
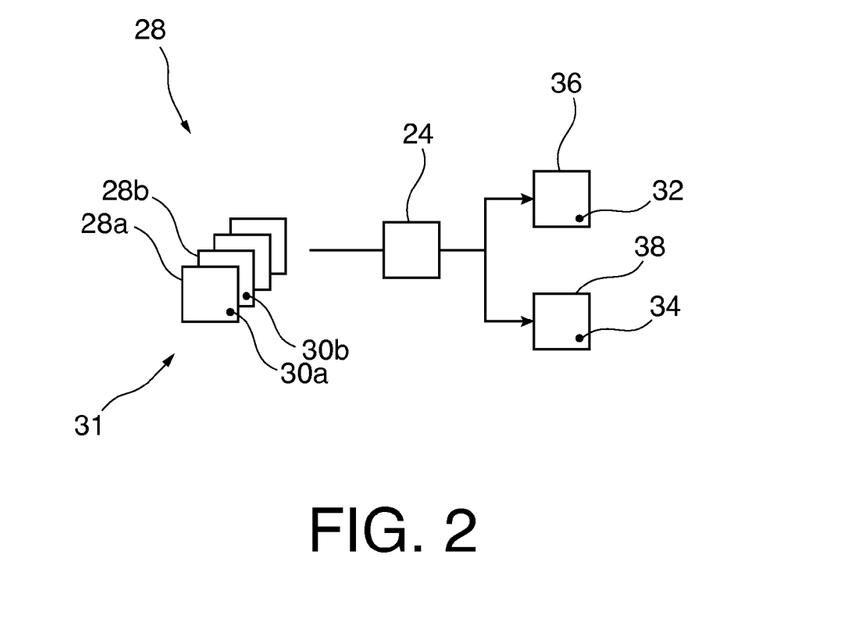
FIG. 2 schematically shows a processing unit according to an embodiment of the invention

FIG. 2 shows the processing of the image data 28 in the processing unit 24. The image data 28 detected are obtained by the detector 18 comprises at least two sets of image data 28a, 28b that are related to different measurement modes. Each image data 28a, 28b comprises measurement signal values 30a, 30b for each pixel 31 in the image data 28a, 28b. For example, a measurement signal value 30a, 30b may indicate the intensity of the x-rays at the specific pixel 31 of the detector 18.

For each pixel 31, the processing unit 24 determines an attenuation value 32 and/or a phase value 34 based on the measurement signal values 30a, 30b as will be explained in the following. From the attenuation value 32 and/or the phase values 34, attenuation image data 36 and/or phase image data 38 is reconstructed by the processing unit 24. It has to be noted that is possible that the processing unit 34 only generates attenuation image data 36 or phase image data 38.

The processing unit 24 may comprise a computer with a processor. Software running on the processor and stored in a storage of the processing unit 24 may perform the method as explained in the above and in the following. Also, the image data 28a, 28b and the attenuation image data 36 and phase image data 38 may be stored in the storage of the processing unit 24.

According to an embodiment of the invention, the method for generating attenuation image data 36 and/or phase image data 38 comprises the steps of: receiving first x-ray image data 28a comprising first pixel-wise measurement signal values 30a in the processing unit 24 and receiving second x-ray image data 28b comprising second pixel-wise measurement signal values 30b.

According to an embodiment of the invention, the x-ray system 10 comprises an x-ray source 16, an x-ray detector 18 and a controller 24 adapted for separating the attenuation image data from the phase image data. The x-ray system 10 may be adapted to obtain x-ray image data 28a, 28b with different measurement modes, for example, the x-ray system 10 comprises a CIX or ICX detector 18.

According to an embodiment of the invention, the x-ray detector 18 is adapted to perform different measurement methods, in particular simultaneously.

According to an embodiment of the invention, the x-ray detector 18 is adapted for spectral weighting detected photons in at least two different ways, for example by counting photons, integrating photon energies or by Campbelling photons. Campbelling may be performed by detecting fluctuations in the photon flow and determining an average value of the fluctuations, which is a measure for square of the photon energies.

In the following the theoretical background, on which the functional relationship relating the attenuation value 32 and the phase value 34 to the measurement signal values 30a, 30b is based, will be explained.

The distribution of intensity I and phase $\phi$ in a plane orthogonal to the optical axis A immediately after the object 20 (assumed to be at z=0) can be expressed in terms of a line integral of the complex refraction index n(x, y, z, λ) of the object 20

$$n = 1 - \delta + i\beta$$

as $$I(x,y,z=0,\lambda) = I_0(x,y,\lambda)e^{-M(x,y,z=0,\lambda)}$$

with $$M(x, y, z = 0, \lambda) = \frac{4\pi}{\lambda} \int_{-\infty}^{0} \beta(x, y, z', \lambda) dz'.$$

M is the attenuation function depending on the imaginary part β of the refraction index n. $I_0(x,y,\lambda)$ is the spatial dependent primary spectrum of the x-ray source 16.

The phase function λ of the wave-front is furthermore disturbed according to $$\varphi(x, y, z = 0, \lambda) = -\frac{2\pi}{\lambda} \int_{-\infty}^{0} \delta(x, y, z', \lambda) dz',$$

and depends on the real part δ of the refraction index n. Note that the refraction index n, its real part δ and its imaginary part β depend on the wavelength λ and therefore on the energy of the x-rays.

The phase function φ is not detectable directly but leads to intensity variations if the wave-front propagates further along the optical axis A.

The task is to retrieve both, M and φ, from measurements at z=R, the detector plane. The attenuation value 32 of a specific pixel is based on the attenuation function M at the position x,y of the pixel in the detector plane, and the phase value 34 is based on the phase function φ at the position x,y of the pixel in the detector plane.

The propagation to the detector plane at z=R can be described by Fresnel propagation, or, approximately by the transport of intensity equation $$\frac{I(x, y, R, \lambda)}{I(x, y, 0, \lambda)} - 1 = \frac{R\lambda}{2\pi}\left(-\nabla^2 \varphi(x, y, 0, \lambda) - \nabla\varphi(x, y, 0, \lambda) \cdot \nabla \ln\frac{I(x, y, 0, \lambda)}{I_0(x, y, \lambda)}\right)$$

which can be further simplified if the intensity does not change strongly behind the object in the near field. Under the assumption that $$\frac{I(x, y, R, \lambda)}{I(x, y, 0, \lambda)} - 1 \ll 1 \Rightarrow \frac{I(x, y, R, \lambda)}{I(x, y, 0, \lambda)} - 1 \approx \ln\frac{I(x, y, R, \lambda)}{I(x, y, 0, \lambda)} = \ln\frac{I(x, y, R, \lambda)}{I_0(x, y, \lambda)} - \ln\frac{I(x, y, 0, \lambda)}{I_0(x, y, \lambda)}$$

this results in $$\ln\frac{I(x, y, R, \lambda)}{I_0(x, y, \lambda)} = \ln\frac{I(x, y, 0, \lambda)}{I_0(x, y, \lambda)} + \frac{R\lambda}{2\pi}\left(-\nabla^2 \varphi(x, y, 0, \lambda) - \nabla\varphi(x, y, 0, \lambda) \cdot \nabla \ln\frac{I(x, y, 0, \lambda)}{I_0(x, y, \lambda)}\right) =$$

$$-M(x, y, 0, \lambda) - \frac{R\lambda}{2\pi}(\nabla^2 \varphi(x, y, 0, \lambda) + \nabla\varphi(x, y, 0, \lambda) \cdot \nabla M(x, y, 0, \lambda))$$

be known. In the absence of absorption K-edges in the object and for a reasonably small energy range with mean wavelength $\lambda_0$, this dependence is given by $$\beta(\lambda) = \left(\frac{\lambda}{\lambda_0}\right)^{p+1} \beta(\lambda_0)$$

$$\delta(\lambda) = \left(\frac{\lambda}{\lambda_0}\right)^{2} \delta(\lambda_0)$$

where p is 3 for small energies where the Compton effect can be neglected and p is smaller for higher energies. Using $\sigma = \lambda/\lambda_0, \gamma = R\lambda/2\pi$ and omitting the spatial coordinates for the sake of compactness we arrive at $$\ln\frac{I(\lambda)}{I_0(\lambda)} = -\sigma^p M(\lambda_0) - \gamma(\sigma\nabla^2 \varphi(\lambda_0) + \sigma^{p+1}\nabla\varphi(\lambda_0) \cdot \nabla M(\lambda_0))$$

This equation needs to be transformed again to provide the expected intensities for a given wavelength:

$$I(\lambda) = I_0(\lambda)\exp(-\sigma^p M(\lambda_0) - \gamma(\sigma\nabla^2 \phi(\lambda_0) + \sigma^{p+1}\nabla\phi(\lambda_0) \cdot \nabla M(\lambda_0)))$$

The measurement signal values 30a, 30b are then $$S_i = \int_\lambda \Phi_i(\lambda) I_0(\lambda) e^{-\sigma^p M(\lambda_0) - \gamma(\sigma\nabla^2 \varphi(\lambda_0) + \sigma^{p+1}\nabla\varphi(\lambda_0) \cdot \nabla M(\lambda_0))} d\lambda$$

wherein a spectral sensitivity function Φ models the data acquisition of the detector 18. The index i shows that there are different functional relationships for different measurement modes.

For example, the most common dependencies for different measurement modes are $$\Phi_i(\lambda) = \begin{cases} 1 & \text{for a counting detector} \\ 1/\lambda & \text{for an integrating detector} \\ 1/\lambda^2 & \text{for a detector in Campbell mode} \end{cases}.$$

The term $$\sigma^{p+1}\nabla\phi(\lambda_0) \cdot \nabla M(\lambda_0)$$

can be neglected, which results in $$S_i = \int_\lambda \Phi_i(\lambda) I_0(\lambda) e^{-\sigma^p M(\lambda_0) - \gamma\sigma\nabla^2 \varphi(\lambda_0)} d\lambda.$$

The last function is a functional relationship or function mapping the attenuation value 32, i.e. M at the mean wavelength $\lambda_0$ and the phase value 34, i.e. $\nabla^2 \phi$ at the mean wavelength $\lambda_0$ to a measurement signal S. This relationship may be evaluated pixel-wise.

The functional relationship depends on the spectral sensitivity function $\Phi_i(\lambda)$ and/or the primary spectrum $I_0(\lambda)$.

The spectral sensitivity function $\Phi_i(\lambda)$ may be obtained by a calibration measurement of the detector 18. Alternatively or additionally, a detector 18 with a known spectral sensitivity function $\Phi_i(\lambda)$ may be used (see above).

Also the primary spectrum $I_0(\lambda)$ may be determined with a calibration measurement.

Only two independent measurements 30a, 30b for S may be required to derive the two quantities $M(\lambda_0)$ and $\nabla^2 \phi (\lambda_0)$ by solving the above functional relationship.

Different possibilities of generating attenuation image data 36 and phase image data 38 from at least two sets of image data 28a, 28b will be explained with respect to FIG. 3 and FIG. 4.

According to an embodiment of the invention, the method comprises the step of: determining attenuation image data 36 comprising pixel-wise attenuation values 32 and/or phase image data 38 comprising pixel-wise phase values 34 from the first and second x-ray image data 28a, 28b by determining a phase value 34 at a pixel 31 from a first measurement signal value 30a obtained in a first measurement mode at the pixel 31 and a second measurement signal value 30b obtained in a second measurement mode at the pixel 31.

According to an embodiment of the invention, the image data 36 and/or 38 are obtained based on a functional relationship mapping an attenuation value 32 and a phase value 34 to a first measurement signal value 30a and a second measurement signal value 30b. The functional relationship depends on the first measurement mode and second measurement mode, for example on the spectral sensitivity function $\Phi_i$ of the detector 18 used for measuring in the respective mode.

According to an embodiment of the invention, the functional relationship is based on a pixel-wise function mapping the attenuation value 32 and/or the phase value 34 to a measurement signal value S.

Figure 3:
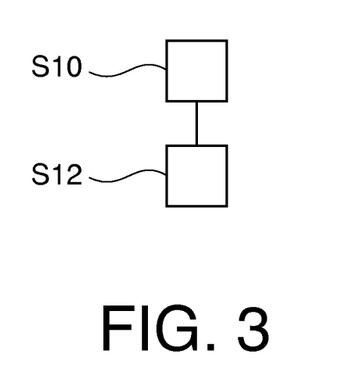
FIG. 3 shows a flow diagram for controlling an x-ray system according to an embodiment of the invention.

With respect to FIG. 3, the image data 36, 38 is determined based on numerical solving the above functional relationship.

In step S10 a diagnostic scan is performed, which results in at least two sets of image data 28a, 28b. In particular, the first image data 28a is obtained in a first measurement mode and the second image data 28b is obtained in a second measurement mode. For example, the first and second image data 28a, 28b may be obtained with a counting detector 18, an integrating detector or a Campbelling detector 18 and the second image data 28b is obtained with an integrating detector.

The first x-ray image data 28a and the second x-ray image data 28b may be obtained or may be detected without moving a mechanical component of the detector 18 or the x-ray system 10. The two sets of image data 28a, 28b may be detected simultaneously.

Also the first and second image data 28a, 28b may be obtained at different energy levels, for example with a spectroscopic detector 18.

From a clinical perspective, it may be further desirable that the two image data 28a, 28b are acquired simultaneously to be insensitive to patient motion. A simultaneous acquisition of image data 28a, 28b at different energies is possible using a spectroscopic detector or using a detector that is adapted to perform the above mentioned measurement modes during one measurement, like the above mentioned CIX or ICX detector 18.

According to an embodiment of the invention, the method comprises the step of: obtaining the first x-ray image data 28a and the second x-ray image data 28b simultaneously with one detector 18 adapted for detecting photons with different spectral weightings.

According to an embodiment of the invention, the first x-ray image data 28a was obtained in a first measurement mode and the second x-ray image data 28b was obtained in a second measurement mode different from the first measurement mode.

According to an embodiment of the invention, the first x-ray image data 28a was obtained with a first spectral weighting of photon energies and the second x-ray image data 28b was obtained with a second spectral weighting different from the first spectral weighting. Spectral weighting may be seen as a measurement method that accounts in a different way for photons with different energies.

According to an embodiment of the invention, the first and second spectral weightings comprise counting photons, integrating photon energies or determining photon energy fluctuations.

In step S12, the image data 28a, 28b is received in the processing unit 24 and processed for generating the image data 36, 38.

For each pixel, the processing unit 24 inserts the first measurement signal value 30a, the spectral sensitivity function $\Phi_1(\lambda)$ for the first measurement mode and the primary spectrum $I_0(\lambda)$ for the first energy level in the functional relationship to get a first equation for the two unknown values 32, 34.

Analogously, the processing unit 24 inserts the second measurement signal value 30a, the spectral sensitivity function $\Phi_2(\lambda)$ for the second measurement mode and the primary spectrum $I_0(\lambda)$ for the second energy level in the functional relationship to get a second equation for the two unknown values 32, 34.

The two equations may be numerically solved by the processing unit 34 the determine the values 32, 34.

According to an embodiment of the invention, the functional relationship depends on a (spectral) sensitivity function $\Phi_i$ weighting photon energies. The first and second measurement modes may comprise different spectral weightings with different spectral sensitivity functions $\Phi_i$.

According to an embodiment of the invention, the phase value (34) is determined based on at least two (spectral) sensitivity functions $\phi i(\lambda)$ modeling the first and second measurement modes. In particular, a (spectral) sensitivity function $\phi i(\lambda)$ may model the weighting of the detector 18 of photon energies in a specific measurement mode.

According to an embodiment of the invention, the attenuation value 32 and the phase value 34 are determined by numerically inverting the functional relationship.

The attenuation image data 36 is generated from the attenuation values 32 of all pixels and the phase image data 38 is generated from the phase values 34 of all pixels. Here, the Laplace operation $\nabla^2$ may be inverted to get the phase image data 38.

Figure 4:
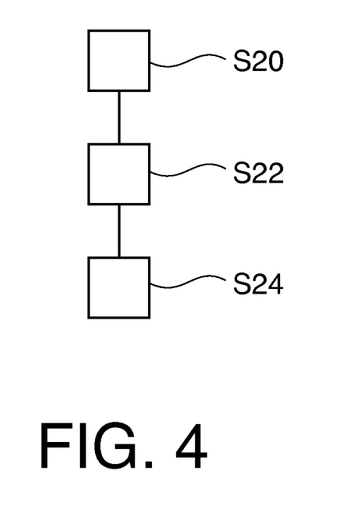
FIG. 4 shows a flow diagram for controlling an x-ray system according to an embodiment of the invention.

With respect to FIG. 4, the image data 34, 36 is determined based on an empiric model.

In step S20, a calibration scan is performed. In this step an object with known refraction indexes n is placed between the x-ray source 16 the detector 18 and measurements are performed. The measurements are evaluated and from these measurements an empiric model is determined. For each measurement mode, the empiric model may model a function mapping a first and a second measurement signal value to an attenuation value and a phase value. The empiric model may be based on a lookup table.

The measurements during the calibration scan may have to be performed for the same measurement modes that should be evaluated during the following data analysis.

It has to be noted that a calibration scan may be performed only once, while the following diagnostic scan may be performed several times with the same calibration data generated during the calibration scan.

In step S22 a diagnostic scan is performed analogously to the step S10 of FIG. 3, which results in first image data 28a obtained in a first measurement mode and second image data 28b obtained in a second measurement mode.

In step S24, the image data 28a, 28b is received in the processing unit 24 and processed for generating the image data 36, 38. For each pixel, the first measurement value 30a and the second measurement value 30b is input to the empirical model for determining the attenuation value 32 and the phase value 34.

According to an embodiment of the invention, the functional relationship is based on an empiric model interrelating the attenuation value 32 and the phase value 34 to a measurement signal value 30a, 30b based on a measurement mode.

According to an embodiment of the invention, the empiric model is determined with a calibration measurement.

Figure 5:
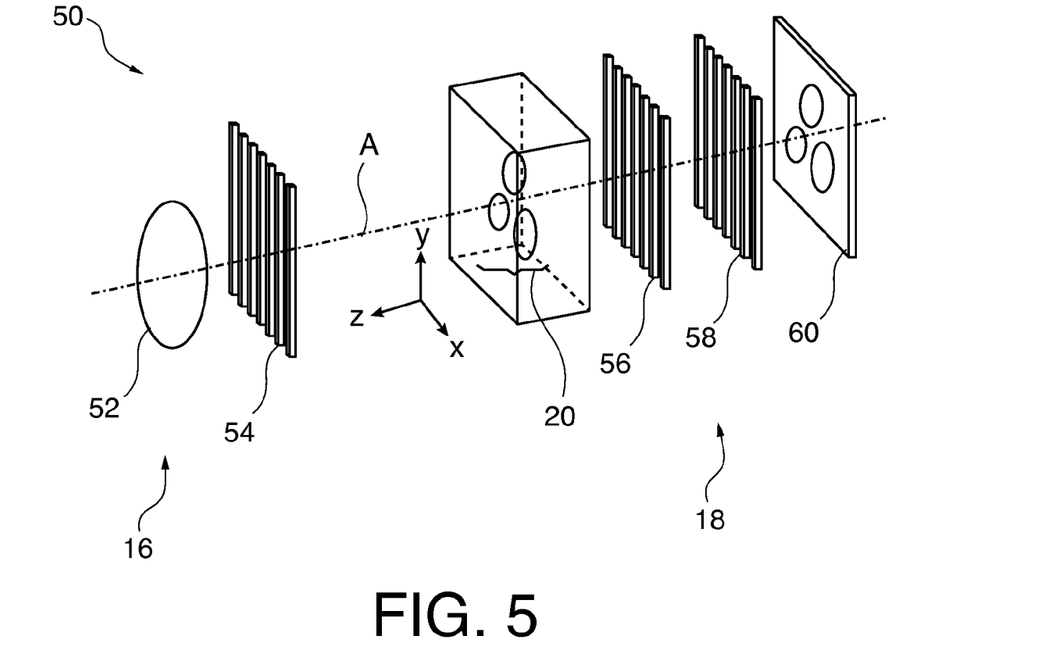
FIG. 5 schematically shows a differential phase imaging system.

The method as described in the above and the following may also be performed with a differential phase imaging system 50 as shown in FIG. 5. The main benefit of the proposed method may be that it does not require mechanical phase stepping during the object scan anymore. Thus, scan speed may be improved by an order of magnitude. Furthermore, the method may be used for tomography with a continuously moving source detector arrangement.

FIG. 5 schematically shows a differential phase imaging system 50 with an x-ray source 16 and a detector 18.

The x-ray source 16 may comprise an incoherent x-ray source 52, for example an x-ray tube 52, and a source grating 54 for achieving spatial beam coherence. The detector 18 may comprise a phase grating 56, an absorber grating 58 and an x-ray detector element 60 adapted for detecting image data 28a, 28b from x-rays emanated from the x-ray source 16 through the object 20.

The phase grating 56 serves as a phase-shifting beam splitter, which transforms the variation of the phase front of the x-ray beam into an intensity modulation, i.e., an interference pattern with a typical length scale of half the pitch of the phase grating 56 at the location of the absorber grating 58. The absorber grating 58 generates a Moire interference pattern from the x-rays leaving the phase grating 56. The Moire interference pattern on the detector element 60 contains information about the phase shift of the deflected and phase-shifted x-rays after passing both the object 20 and the phase grating 56.

Instead of moving one of the gratings 54, 56, 58, in the following a method of generating attenuation image data 36 and phase image data 38 is described that uses different energy levels for obtaining the x-ray image data 28a, 28b. The method may be seen as a calibration and processing scheme for differential phase contrast CT. For example, an energy selective detector element 60 may be used.

As the phase stepping may require high mechanical precision and may increase the scan time, the avoidance of mechanical stepping may result in an faster tomographic setup. Also a continuously rotating system may be realized.

In the following the theoretical background with respect to a DPCI system 50E, on which the functional relationship relating the attenuation value 32 and the phase value 34 to the measurement signal values 30a, 30b is based, will be explained.

As already said, the refraction index n is wavelength and energy dependent.

$$n = 1 - \delta + i\beta$$

Using the projection approximations, the intensity of an x-ray beam is attenuated by the object according to $$I(E) = I_0(E) e^{-\int \mu(E,\vec{x}) ds} = I_0(E) e^{-\frac{4\pi E}{ch} \int \beta(E,\vec{x}) ds}$$

The phase of the wave-front is furthermore disturbed according to $$\varphi(E) = -\frac{2\pi E}{hc} \int \delta(E, \vec{x}) ds$$

where all the integrations are performed along the geometric path of the x-ray. Suppose the systems design energy is $E_0$. The intensity variation in each pixel 31 as a function of the relative position ξ of the grids 56 and 58 (normalized to 1) may be modeled as $$I(\xi, E_0) = A_0 (\cos(2\pi\xi + \Phi_0) + 1)$$

where Φ is the gradie $$I(\xi, E_0) = A_0 (\cos(2\pi\xi + \Phi_0) + 1)_e$$

grating orientation. The quantity $A_0$ is equal to the mean intensity $I(E_0)$.

In order to illustrate the basic idea of the proposed processing scheme, we first describe an idealized case with perfect grids and rather low x-ray energies (the more complicated general scheme will be outlined afterwards): We first recall that the refractive index has a in the absence of K-edges and for reasonably small energies (where Compton scatter can be neglected) the energy dependence $$\mu(E) = \left(\frac{E_0}{E}\right)^3 \mu(E_0)$$

$$\delta(\lambda) = \left(\frac{E_0}{E}\right)^2 \delta(E_0)$$

Using these relations, we can conclude that $$I(\xi, E) = A_0^{(E_0/E)^3} \left( \cos\left(2\pi\xi + \Phi_0 \frac{E_0}{E}\right) + 1 \right).$$

Knowing this relation, it is possible to estimate the quantities of interest, viz., $A_0$ and $\Phi_0$ from a view intensities at different energies but each time with ξ=0. Note that in the above equation, the amplitude $A_0$ is already normalized to the air (calibration) scan in order to compensate for different intensities of the incident x-ray beam at different energies.

In a real system, the model for the dependence of the intensity as a function of grid-displacement may not be met well. In particular, the x-ray beam may be partially incoherent, the grid 56 may not be a perfect phase grid that imposes a phase shift of π, the gird 58 may not absorb x-rays perfectly, and the spectral response of the detector 60 may not be perfect.

All these effects may be compensated by executing the conventional grid stepping during a calibration scan. More specifically, during this calibration scan, the functional dependence of the intensity as a function of the grid displacement is measured. The resulting function $g_E$ may depend on the energy bin, which is reflected by the subscript E:

$$I(\xi, E) = A g_E(2\pi\xi + \Phi)$$

Since we have a priori knowledge that $g_E$ is periodic, it will be desired to expand the measured values in a finite Fourier series. Another important complication may arise for higher energies, namely the energy dependence of the absorption coefficient becomes more complicate. It is common to separate the total absorption into the contribution of the photo- and the Compton-effect.

$$I(\xi) = I_0(E) e^{B_{photo}(E_0/E)^3 + B_{Compton} f_{KN}(E)} g_E\left(2\pi\xi + \Phi_0 \frac{E_0}{E}\right)$$

This equation provides the functional relationship relating the phase value with an intensity value 30a, 30b or a measurement signal value 30a, 30b. The equation may be seen as a forward model that connects the desired phase gradient $\Phi_0$ at the reference energy E with the measured data I. Note that $\xi$ is the relative position of the grids 56 and 58 and may be set to 0.

Figure 6:
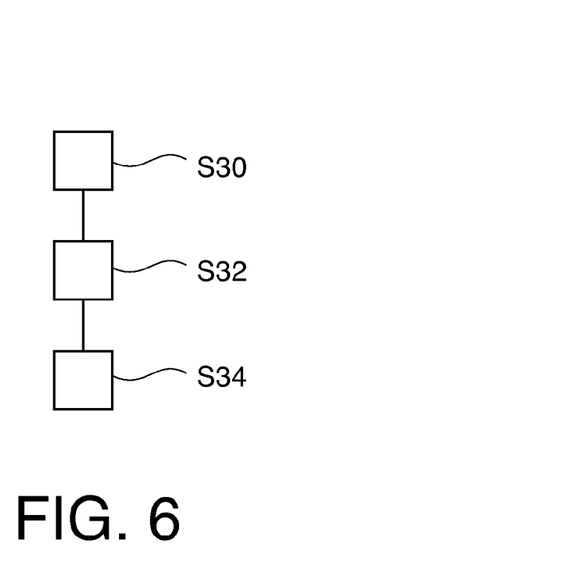
FIG. 6 shows a flow diagram for controlling an x-ray system according to an embodiment of the invention.

FIG. 6 shows a flow diagram for a method for determining phase image data 38.

In step S30 a calibration scan is performed. In this scan, the sensitivity function $g_E$ is measured or determined. Note that the gratings 56, 58 need not be moved in the calibration scan. In particular, the function $g_E$ may be determined by determining a Finite Fourier series by fitting its Fourier coefficients with measurements of intensities at different energies. Additional fit parameters are the parameters $B_{photo}$ and $B_{Compton}$. These parameters and the Finite Fourier series may be seen as an empiric model of the detector 18.

In step S32 a diagnostic scan is performed. During the diagnostic scan, the intensities $I(0, E_i)$ are measured for a couple of energies $E_i$ (for example at least two energies $E_i$). For each energy $E_i$ x-ray image data 28a, 28b is generated. Note that the gratings 56, 58 need not be moved in the diagnostic scan.

According to an embodiment of the invention, the first x-ray image data 28a is obtained at a first energy level $E_1$ and the second x-ray image data 28b is obtained at a second energy level $E_2$ different from the first energy level $E_1$.

According to an embodiment of the invention, the method comprises the steps of: obtaining the first x-ray image data 28a with a grating based differential phase imaging system 50 at a first energy level $E_1$; and obtaining the second x-ray image data 28a with the grating based differential phase imaging system 50 at a second energy level $E_2$ and at the same grating positions.

In step S34, the x-ray image data 28a, 28b generated during the diagnostic scan is received in the processing unit 34 and evaluated to generate phase image data 38.

The above described functional relationship with the determined function $g_E$ is used for determining the phase value 34 or $\Phi_0$ at the pixel 31 from the measurement signal values 30a, 30b obtained at the pixel 31 at different energies $E_i$. For example, the resulting equations may be numerically inverted.

According to an embodiment of the invention, the phase value 34 is determined based on a (spectral) sensitivity functions $g_E$ modeling the energy behavior of the detector 18.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method for generating phase image data, the method comprising acts of:
    obtaining first x-ray image data comprising first pixel-wise measurement signal values by an x-ray detector operating in a first measurement mode;
    obtaining second x-ray image data comprising second pixel-wise measurement signal values by the x-ray detector operating in a second measurement mode different from the first measurement mode; and
    determining the phase image data comprising pixel-wise phase values from the first and the second x-ray image data by determining a phase value at a pixel from a first measurement signal value obtained in the first measurement mode at the pixel and a second measurement signal value obtained in the second measurement mode at the pixel, wherein the x-ray detector configured to simultaneously operate in the first and the second measurement modes to simultaneously perform the act of obtaining first x-ray image data and the act of obtaining second x-ray image data with different spectral weightings such that the first x-ray image data is obtained with a first spectral weighting simultaneously with the second x-ray image data which is obtained with a second spectral weighting different from the first spectral weighting; and
    generating an output that includes the determined phase image data.

2. The method of claim 1, wherein the determining act determines the phase value based on a sensitivity function modeling an energy behavior of a measurement mode, wherein the sensitivity function includes a first sensitivity function modeling the energy behavior of the first measurement mode and a second sensitivity function modeling the energy behavior of the second measurement mode, the second sensitivity function being different from first sensitivity function.

3. The method of claim 1, wherein the first and the second spectral weightings comprise one of counting photons, integrating photon energies and determining photon energy fluctuations.

4. The method of claim 1, wherein the determining act determines the phase value by numerical inverting an equation system for the phase value, and the first and the second measurement signal values.

5. The method of claim 1, wherein the determining act determines the phase value based on an empiric model interrelating the phase value to the first and the second measurement signal values based on the first and the second measurement modes.

6. The method of claim 1, further comprising an act of:
determining an attenuation value at the pixel from the first measurement signal value obtained in the first measurement mode at the pixel and the second measurement signal value obtained in the second measurement mode at the pixel.

7. The method of claim 1,
wherein the detector is configured to detect photons with the different spectral weightings.

8. The method of claim 1, wherein the act of obtaining the first x-ray image data obtains the first x-ray image data at a first energy level and the act of obtaining the second x-ray image data obtains the second x-ray image data at a second energy level different from the first energy level.

9. The method of claim 1, further comprising acts of:
obtaining the first x-ray image data with a grating based differential phase imaging system at a first energy level with gratings located at grating positions; and
obtaining the second x-ray image data with the grating based differential phase imaging system at a second energy level and with the gratings located at the grating positions.

10. A non-transitory computer readable medium comprising computer instructions for generating phase image data, which, when being executed by a processor, configure the processor to perform act of:
causing an x-ray detector operating in a first measurement mode to obtain first x-ray image data comprising first pixel-wise measurement signal values;
simultaneously with the causing act, causing the x-ray detector to simultaneously operate in a second measurement mode to simultaneously obtain second x-ray image data comprising second pixel-wise measurement signal values, the second measurement mode being different from the first measurement mode, wherein the first x-ray image data is obtained with a first spectral weighting simultaneously with the second x-ray image data which is obtained with a second spectral weighting different from the first spectral weighting; and
determining the phase image data comprising pixel-wise phase values from the first and the second x-ray image data by determining a phase value at a pixel from a first measurement signal value obtained in the first measurement mode at the pixel and a second measurement signal value obtained in the second measurement mode at the pixel; and
generating an output that includes the determined phase image data.

11. An x-ray system comprising:
an x-ray source;
an x-ray detector; and
a controller;
wherein the x-ray detector is configured simultaneously to operate in a first measurement mode to obtain first x-ray image data comprising first pixel-wise measurement signal values, and to operate in a second measurement mode different am the first measurement mode to obtain second x-ray image data comprising second pixel-wise measurement signal values, and
wherein the controller is configured to determine phase image data comprising pixel-wise phase values from the first and the second x-ray image data by determining a phase value at a pixel from a first measurement signal value obtained by the detector in the first measurement mode at the pixel and a second measurement signal value obtained simultaneously with the first measurement signal value by the detector in the second measurement mode at the pixel with different spectral weightings such that the first x-ray image data is obtained with a first spectral weighting simultaneously with the second x-ray image data which is obtained with a second spectral weighting different from the first spectral weighting,
wherein the controller is further configured to generate the phase image data based on the first and the second x-ray image data simultaneously obtained by the detector operating simultaneously in the first and the second measurement modes.

12. The x-ray system of claim 11, wherein the first and the second spectral weightings comprise one of counting photons, integrating photon energies and determining photon energy fluctuations.

13. The x-ray system of claim 11, wherein the x-ray detector is configured to simultaneously spectrally weight detected photons in at least two different ways selected from the group consisting of counting photons, integrating photon energies and Campbelling photons.

14. The x-ray system of claim 11, wherein the controller is configured to determine the phase value based on a sensitivity function modeling an energy behavior of a measurement mode, wherein the sensitivity function includes a first sensitivity function modeling the energy behavior of the first measurement mode and a second sensitivity function modeling the energy behavior of the second measurement mode, the second sensitivity function being different from first sensitivity function.

15. The x-ray system of claim 11, wherein the controller is configured to determine the phase value by numerical inverting an equation system for the phase value, and the first and the second measurement signal value.

16. The x-ray system of claim 11, wherein the controller is configured to determine the phase value based on an empiric model interrelating the phase value to the first and the second measurement signal values based on the first and the second measurement modes.

17. The x-ray system of claim 11, wherein the controller is further configured to determine an attenuation value at the pixel from the first measurement signal value obtained in the first measurement mode at the pixel and the second measurement signal value obtained in the second measurement mode at the pixel.

18. The x-ray system of claim 11, wherein the controller is further configured to detect photons with the different spectral weightings.

* * * * *